United States Patent [19]

Strauch et al.

[11] Patent Number: 5,276,268
[45] Date of Patent: Jan. 4, 1994

[54] PHOSPHINOTHRICIN-RESISTANCE GENE, AND ITS USE

[75] Inventors: Eckhard Strauch; Walter Arnold; Renate Alijah; Wolfgang Wohlleben; Alfred Pühler, all of Bielefeld; Peter Eckes, Kelkheim/Taunus; Gunter Donn, Hofheim am Taunus; Eugen Uhlmann, Glashutten/Taunus; Friedrich Hein, Munich; Friedrich Wengenmayer, Hofheim am Taunus, all of Fed. Rep. of Germany

[73] Assignee: Hoechst Aktiengesellschaft, Frankfurt am Main, Fed. Rep. of Germany

[21] Appl. No.: 736,316

[22] Filed: Jul. 29, 1991

Related U.S. Application Data

[63] Continuation-in-part of Ser. No. 501,314, Mar. 26, 1990, abandoned, which is a continuation of Ser. No. 145,302, Jan. 19, 1988, abandoned, and a continuation of Ser. No. 605,131, Oct. 31, 1990, abandoned, which is a continuation of Ser. No. 88,118, Aug. 21, 1987, abandoned.

[30] Foreign Application Priority Data

| | | |
|---|---|---|
| Aug. 23, 1986 [DE] | Fed. Rep. of Germany | 3628747 |
| Nov. 3, 1986 [DE] | Fed. Rep. of Germany | 3637307 |
| Dec. 16, 1987 [DE] | Fed. Rep. of Germany | 3642829 |
| Jan. 8, 1987 [DE] | Fed. Rep. of Germany | 3700313 |
| Jan. 21, 1987 [DE] | Fed. Rep. of Germany | 3701624 |
| Nov. 7, 1987 [DE] | Fed. Rep. of Germany | 3737918 |

[51] Int. Cl.$^5$ .................. A01H 4/00; C12N 5/14; C12N 15/31; C12N 15/82
[52] U.S. Cl. .................. 800/205; 435/172.3; 435/240.4; 435/252.3; 800/255; 800/DIG. 43; 536/23.7; 935/67
[58] Field of Search .................. 536/27, 23.7; 435/172.3, 252.3, 253.5; 800/205, 255, DIG. 43; 935/67

[56] References Cited

U.S. PATENT DOCUMENTS

| | | |
|---|---|---|
| 4,769,061 | 9/1988 | Camai . |
| 5,077,399 | 12/1991 | Brauer et al. .................. 536/27 |

FOREIGN PATENT DOCUMENTS

| | | |
|---|---|---|
| 0173327 | 3/1986 | European Pat. Off. . |
| 0242246 | 10/1987 | European Pat. Off. . |
| WO86/02097 | 4/1986 | PCT Int'l Appl. . |
| WO87/05629 | 9/1987 | PCT Int'l Appl. . |

OTHER PUBLICATIONS

Thompson et al., EMBO J. 6(9):2519-23 (1987).
De Block et al., EMBO J. 6(9):2513-18 (1987).
Murakami et al., Mol. Gen. Genet. 205:42-50 (1986).
Ohlrogge et al., Chemical Abstracts 105:55584K (1986).
Howell et al., Phytopathology 69:480-82 (1979).
Grantham et al., Oxford Surveys 3:48-49; 54-61 (1986).
Ikemura, Mol. Biol. Evol. 2(1):13; 26-32 (1985).
Potrykus, Bio/Technology 8:535-542 (1990).
Gelvin, Plant Molecular Biology 8:355-59 (1987).
Vaeck et al., Nature 328:33-37 (1987).
Fischhoff et al., Bio/Technology 5:807-813 (1987).
Vaeck et al., UCLA Symposium on Molecular and Cellular Biology New Series, vol. 62, Plant Gene Systems and Their Biology, Tamarron, Colorado, Feb. 2-8, 1987, pp. 171-181, Alan R. Liss, Inc.
Wohlleben et al., Gene 70:25-37 (1988).
Shah et al., Science 233:478-81 (1986).

Primary Examiner—Che S. Chereskin
Attorney, Agent, or Firm—Finnegan, Henderson, Farabow, Garrett & Dunner

[57] ABSTRACT

The phosphinothricin (PTC)-resistance gene isolated from the genome of Streptomyces viridochromogenes DSM 40736 is, after adaptation to the codon usage in plants, synthesized and incorporated into gene structures which make plants resistant to PTC after expression therein.

14 Claims, No Drawings

![5,276,268]

PHOSPHINOTHRICIN-RESISTANCE GENE, AND ITS USE

This application is a continuation-in-part application, combining application Ser. No. 07/501,314, filed Mar. 26, 1990, now abandoned which is a continuation of U.S. Ser. No. 07/145,302, filed Jan. 19, 1988, now abandoned and application Ser. No. 07/605,131, filed Oct. 31, 1990, now abandoned, which is a continuation of U.S. Ser. No. 07/088,118 filed Aug. 21, 1987, now abandoned.

Phosphinothricin (PTC, 2-amino-4-methylphosphinobutyric acid) is an inhibitor of glutamine synthetase. PTC is a "structural unit" of the antibiotic phosphinothricyl-alanyl-alanine. This tripeptide (PTT) is active against Gram-positive and Gram-negative bacteria as well as against the fungus *Botrytis cinerea* (Bayer et al., Helv. Chim. Acta 55 (1972) 224). PTT is produced by the strain *Streptomyces viridochromogenes* Tu 494 (DSM 40736, DSM 4112).

German Patent, 2,717,440 discloses that PTC acts as a total herbicide. The published PCT Application WO 86/02097 describes plants whose resistance to PTC is attributable to overproduction of glutamine synthetase. Overproduction of this type, for example resulting from gene amplification, entails the risks of instability. Hence, such an instability would be associated with a decrease in the overproduction of glutamine synthetase, and the competitive inhibitory action of PTC would reappear.

In contrast, the invention, which is defined in the patent claims, relates to a PTC-resistance gene and to its use for the production of PTC-resistant plants. In addition, this gene can also be used as a resistance marker. Furthermore, the gene is suitable for the selective N-acetylation of the L-form of racemic PTC.

BRIEF DESCRIPTION OF THE TABLES

Table I depicts DNA Sequence I which was obtained by sequencing the 0.8 Kb BglII fragment containing the PTC-resistance gene. The Shine-Delgarno sequence (AGGAA) and the start condon (GTG) are underlined.

Table II contains DNA Sequence II which depicts the restriction sites within the sequenced gene. Enzymes which cut the sequence more than six times are not identified.

Table III contains DNA Sequence III (and its corresponding amino acid sequence), depicting a modified PTC-resistance gene which is optimized, by de novo synthesis, to a codon usage favorable for the plant RNA, polymerase II.

Table II contains amino acid and DNA Sequence IV which show the plan of synthesis for making DNA Sequence III.

The PTC-resistance gene according to the invention can be obtained by cutting, with BamHI, the total DNA from *Streotomyces viridochromogenes* DSM 4112 (deposition under the Budapest Treaty) or DSM 40736 (general collection) which has been selected for phosphinothricyl-alanyl-alanine (PTT)-resistance, by cloning a fragment of 4.0 kb in size, and by selection for PTT resistance. The restriction map details the characteristics of this 4.0 kb fragment.

Cloning experiments on sections of this 4 kb fragment were carried out to localize the position of the coding region more accurately. It emerged from this that the resistance gene is located on the 1.6 kb SstII-SstI fragment. Digestion with BclII resulted in the fragment which is 0.8 kb in size and which, after incorporation into a plasmid and transformation of *S. lividans*, confers PTT resistance. This resistance is caused by N-acetylation of PTC. Hence the resistance gene codes for an acetyltransferase.

Maxam and Gilbert sequencing of the 0.8 kb fragment reveals DNA sequence I (Table 1). The position of the resistance gene can be determined from the open reading frame of this sequence (from position 258). The end of the gene is located at the penultimate nucleotide shown (position 806), i.e. the last nucleotide (position 807) is the first of the stop codon.

The Shine-Dalgarno sequence in DNA sequence I is emphasized by underlining, as is the GTG acting as start codon. Thus, the top line depicts the definitive reading frame.

DNA sequence II (Table II) shows the restriction sites within the sequenced gene. Enzymes which cut the sequence more than six times are not indicated.

The antibiotic PTT is taken up by bacteria and broken down to PTC. The latter also inhibits glutamine synthetase in bacteria, so that the bacteria die of a lack of glutamine. Hence, PTT-producing bacteria ought to have a mechanism which protects them from the action of PTT, that is to say either prevents reuptake of the PTT which has been produced or permits a modification of the breakdown product PTC. However, surprisingly, the PTT producer *S. viridochromogenes* DSM 4112 is sensitive to its own antibiotic. Unexpectedly, it proved possible, however, by selection for PTT resistance to find, at the surprisingly high rate of $10^{-5}$, selectants which are resistant to PTT and, moreover, suppress the background growth of adjacent colonies.

A gene bank was set up from the DNA of these selectants by isolating the DNA and cleaving it with BamHI and ligating it into a Streptomycetes vector. The ligation mixture was transformed into the commercially available strain *S. lividans* TK 23, resulting in about 5000 to 10000 transformants having an insert of about 1 to 5 kb per 1 μg of ligation mixture. Among the transformants there were PTT-resistant *S. lividans* strains. It was possible, by isolation of the plasmids and retransformation into *S. lividans*, to show that the resistance is plasmid-coded. The gene responsible for the resistance is located on a 4 kb BamHI fragment. The coding region is located on the 0.8 kb BclII fragment. The BamHI fragment contains no cleavage sites for the enzymes ClaI, EcoRI, EcoRV, HindIII, HpaI, KpnI, PvuI, PvuII and XhoI.

Comparison with the restriction map of a resistance gene, which has not been characterized in detail, for *S. hygroscopicus* FERM BP-130/ATCC 21705 (European Patent Application with the publication no. 0,173,327, FIG. 7) shows that the resistance gene according to the invention differs from the known gene, which was found during the search for PTT biosynthesis genes.

It was possible to show, by incubation of cell extracts from *S. viridochromogenes* DSM 4112 and *S. lividans* TK 23 on the one hand, and the PTT-resistant *S. viridochromogenes* selectants and a plasmid-carrying *S. lividans* transformant, on the other hand, with PTC and acetyl-coenzyme A that the latter cells have acetylating activity. Chromatography tests show that the acetylation takes place on the amino group.

Since PTT-resistance has also been found in *E. coli*, and thus the resistance mechanism also functions in Gram-negative bacteria, it is possible to rule out resistance based on transport phenomena. Thus, after coupling to plant promoters and using suitable vectors, the resistance gene according to the invention can be transformed into plants, and in this way PTC-resistant plants can be produced.

The N-acetylation of PTC can also be used for racemate resolution of synthetic D,L-PTC since selective acetylation of only the L-form takes place.

Thus the invention also relates to the use of the resistance gene for the selective N-acetylation of the L-form of racemic PTC.

The PTC acetyltransferase coded for by the resistance gene according to the invention can thus be used to separate racemic PTC, as can be obtained, for example, by the method of German Patent 2,717,440, into the optical antipodes by exposing the racemate to the acetylating action of this enzyme, since there is selective attack on the L-form while the D-form remains unchanged. The mixture thus obtained can then be fractionated in a manner known per se on the basis of the differences in properties.

The contacting of N-acyl-D,L-amino acids with acylases, which are immobilized on carriers where appropriate, with selective liberation of the L-amino acid, which can be extracted with water-immiscible solvents from the mixture with the N-acyl-D-amino acid after acidification, has been disclosed (British Patent 1,369,462). A corresponding fractionation of N-acyl-D,L-PTC is disclosed, for example, in German Offenlegungsschrift 2,939,269 or U.S. Pat. No. 4,226,941.

The D-PTC which remains according to the invention can be racemized in known manner (European Patent Application with the publication no. (EP-A) 0,137,371, example 8), and then returned to the process.

It is possible, but not necessary, to isolate the enzyme, this also being intended to mean, here and hereinafter, always the enzymatically active part. If the enzyme is isolated, it can be used in the free form or the form immobilized on a carrier. Examples of suitable carriers are described in EP-A 0,141,223. However, it is expedient not to isolate the enzyme but to use any desired PTC-resistant cells which express the enzyme according to the invention. Thus, it is possible and expedient to use the PTT-resistant selectants of *S. viridochromogenes* DSM 4112. Moreover, it is possible and advantageous to use any desired cell which has been transformed with the gene according to the invention and which is able to express PTC acetyltransferase. In this connection, the gene according to the invention, this also being intended to mean active parts thereof, can be introduced into the host cell in plasmid-integrated form or by using other customary methods of gene manipulation, for example by transfection. For example, incorporation into an *E. coli* expression plasmid and transformation of *E. coli* with such a plasmid is expedient, for example by the methods known from EP-A 0,163,249 and 0,171,024.

For the N-acetylation, according to the invention, of L-PTC in the racemate the cells which express PTC acetyltransferase can be used in the free or immobolized form, with the customary methods of immobilization being used (for example German Offenlegungsschrift 3,237,341 and literature cited therein).

The enzymatic acetylation, according to the invention, of L-PTC is carried out in the manner customary for enzymatic reactions, with the conditions of the method being governed by the characteristics of the organism used. In principle, methods suitable for this are the same as for the above-mentioned selective deacylation method.

Genes from Streptomycetes have a very high proportion of G+C, the adenine (A)+thymine (T) : guanine (G)+cytosine (C) ratio being about 30:70. The proportion of GC in plant genes is far lower, being about 50%. For this reason, in a further development of the inventive idea, the DNA sequence of the resistance gene has been optimized, by de novo synthesis, to a codon usage favorable for plant RNA polymerase II.

The invention relates to a modification of the resistance gene as discussed above which is proposed in German Patent Application P 36 28 747.4 and the additional application P 36 42 829.9, namely an adaptation to the codon usage in plants. The corresponding amino acid sequence is depicted in DNA Sequence III. Further embodiments of the invention are defined in the patent claims or are explained hereinafter.

As is known, the genetics code is degenerate, i.e., only 2 amino acids are coded for by a single triplet, whereas the remaining 18 genetically codable amino acids are assigned to 2 to 6 triplets. Thus, theoretically, a wide variety of codon combinations can be chosen for the synthesis of the gene. Since the said relative proportion of the individual nucleotides in the total DNA sequence exerts an influence, it was used as one of the criteria on which the sequence optimization was based.

The following modifications were made to the sequenced gene:

1. The Streptomycetes gene start codon GTG (position 258-260 in the sequence in DNA Sequence I was replaced by the start codon ATG which is used by plant RNA polymerase II.

2. Within the gene, the Streptomycetes gene codons were changed in such a way that they resulted in codons suitable in plant genes (G/C ratio).

3. The TGA stop codon was placed at the end of the sequence to terminate the translation process.

4. The beginning and end of the gene sequence were provided with protruding ends of restriction sites in order to be able to amplify the gene and ligate it between plant regulation sequences.

5. Palindromic sequences were reduced to a minimum.

The DNA sequence III according to the invention (with the corresponding amino acid sequence) is depicted in the annex.

Three internal unique cleavage sites for the restriction enzymes XbaI (position 152), BamHI (312) and XmaI (436) make possible the subcloning of part-sequences which can be incorporated in well-investigated cloning vectors such as, for example, pUC18 or pUC19. In addition, a number of other unique recognition sequences for restriction enzymes were incorporated within the gene, and these, on the one hand, provide access to part-sequences of acetyltransferase and, on the other hand, allow modifications to be made:

| Restriction enzyme | Cut after nucleotide No. (codings strand) |
| --- | --- |
| BspMII | 11 |
| SacII | 64 |
| EcoRV | 74 |
| HpaI | 80 |
| AatII | 99 |
| BstXI | 139 |
| ApaI | 232 |
| ScaI | 272 |

-continued

| Restriction enzyme | Cut after nucleotide No. (codings strand) |
| --- | --- |
| AvrII | 308 |
| AflII | 336 |
| StuI | 385 |
| BssHII | 449 |
| FokI | 487 |
| BglI | 536 |
| BglII | 550 |

The construction of part-sequences by chemical synthesis and enzymatic ligation reactions is carried out in a manner known per se (EP-A 0,133,282, 0,136,472, 0,155,590, 0,161,504, 0,163,249, 0,171,024, 0,173,149 or 0,177,827). Details, such as restriction analyses, ligation of DNA fragments and transformation of plasmids in E. coli, are described at length in the textbook of Maniatis (Molecular Cloning, Maniatis et al., Cold Spring Harbor, 1982).

The gene sequence which has been cloned in this way is then introduced into plants, under the control of plant regulation signals, and its expression is induced. EP-A 0,122,791 reviews known methods. In this way are obtained PTC-resistant plant cells (i.e., a selection feature for transformed cells is available), plants or parts of plants and seeds.

The invention is illustrated in detail in the examples which follow. Unless otherwise stated, parts and percentage data relate to weight.

Example 1: PTT-resistant selectants

The strain S. viridochromogenes DSM 4112 was cultured on minimal medium (Hopwood et al., Genetic Manipulation of Streptomyces, A Laboratory Manual, The John Innes Foundation, Norwich, England (1985), page 233) and increasing concentrations of PTT were added. At a concentration of 100 µg/ml one resistant colony was found per $10^5$ colonies, approximately.

Example 2: Preparation of the vector

The plasmid pSVH1 (European Patent 0,070,522; U.S. Pat. No. 4,673,642) is cut with BolII, and the fragment about 7.1 kb in size is isolated and ligated with the 1.1 kb BclI fragment having thiostrepton resistance (European Patent Application with the publication number 0,158,201). The plasmid pEB2 which is about 8.15 kb in size is obtained.

Example 3: Isolation of the resistance gene

The total DNA is isolated from the selectants obtained in example 1, and it is cleaved with BamHI. The plasmid pEB2 is likewise opened with BamHI, and the two mixtures are combined and ligated. The ligation mixture is transformed into S. lividans TK 23 (obtainable from the John Innes Foundation), with 5000 to 10000 transformants having an insert of about 1-5 kb being obtained per 1 µg of ligation mixture. Selection for PTT-resistance produces two resistant S. lividans colonies. The plasmid which has been taken up is isolated from the latter and is cut with BamHI. A 4 kb BamHI fragment which carries the gene responsible for resistance is found. This plasmid was called pPR1.

Retransformation into S. lividans TK 23 shows, that the PTT-resistance is plasmid-coded, since the transformants grow on minimal medium containing 100 µg/ml PTT.

Example 4: Demonstration of the inactivation of PTC by N-acetylation

The following strains were examined to demonstrate the acetylating activity of the cloned fragment: S. viridochromogenes DSM 40736, S. viridochromogens (PTT-resistant mutant), S. lividans TK 23 and S. lividans TK 23 (pPR1).

This entails the strains being inoculated into lysis medium A (European Patent Application with the publication number 0,158,872, page 6) and incubated at 30° C. in an orbital shaker for 2 days. After harvesting, 1 mg of mycelium is disrupted with ultrasound in a suitable buffer (for example RS buffer: C. J. Thompson et al., J. Bacteriol. 151 (1982), 678-685). The procedure for a typical experiment to measure PTC breakdown is as follows:

100 µl of PTC solution (250 µg/ml) and 50 µl of acetyl-CoA (4 mg/ml) are added to 250 µl of crude extract, and the mixture is incubated at 30° C. for 2 hours. The amounts of PTC which are still present after this time are measured by HPLC. The results of this are as follows:

| Strain | unreacted PTC / introduced PTC |
| --- | --- |
| S. lividans TK23 | 100% |
| S. viridochromogenes (DSM 40736) | 72% |
| S. viridochromogenes Selectant | 7% |
| S. lividans TK23 (pPR1) | 31% |

A comparison with reference substances on thin-layer chromatography (no stain with ninhydrin) demonstrates that N-acetylation of the PTC has taken place.

For the next series of examples, the following media were used:

a) for bacteria:

YT medium: 0.5% yeast extract, 0.8% Bacto tryptone, 0.5% NaCl

LB medium: 0.5% yeast extract, 1% Bacto tryptone, 1% NaCl as solid medium: addition of 1.5% agar to each b) for plants M+S medium: see Murashige and Skoog, Physiologica Plantarum 15 (1962) 473

2 MS medium: M+S medium containing 2% sucrose

MSC 10 medium: M+S medium containing 2% sucrose, 500 mg/l cefotaxime, 0.1 mg/l naphthylacetic acid (NAA), 1 mg/l benzylaminopurine (BAP), 100 mg/l kanamycin MSC 15 medium: M+S medium containing 2% sucrose, 500 mg/l cefotaxime, 100 mg/l kanamycin.

5. Chemical synthesis of a single-stranded oligonucleotide

The synthesis of fragment II, one of the four part-fragments I-IV, started from the terminal oligonucleotide IIc (nucleotide No. 219 to 312 in the coding strand of DNA sequence I). For the solid-phase synthesis, the nucleotide at the 3' end, that is to say guanosine (nucleotide No. 312) in the present case, is covalently bonded via the 3'-hydroxyl group to a support. The support material is CPG (controlled pore glass) functionalized with long-chain aminoalkyl radicals. Otherwise, the synthesis follows the known (from the said EP-As) methods.

The plan of synthesis is indicated in DNA sequence IV (Table IV), which otherwise corresponds to DNA sequence III.

6. Enzymatic linkage of the single-stranded oligonucleotides to give gene fragment II For the phosphorylation of the oligonucleotides at the 5' end, 1 nmol of each of oligonucleotides IIb and IIc was treated with 5 nmol of adenosine triphosphate and 4 units of T4 polynucleotide kinase in 20 µl of 50 mM tris-HCl buffer (pH 7.6), 10 mM magnesium chloride and 10 mM dithiothreitol (DTT) at 37° C. for 30 minutes. The enzyme is inactivated by heating at 95° C. for 5 minutes. Oligonucleotides IIa and IId, which form the "protruding" sequence in DNA fragment II, are not phosphorylated. This prevents the formation, during the subsequent ligation, of larger subfragments than correspond to DNA fragment II.

Oligonucleotides II (a-d) are ligated to give subfragment II as follows: 1 mmol of each of oligonucleotides IIa and IId and the 5'-phosphates of IIb and IIc are together dissolved in 45 µl of buffer containing 50 mM tris-HCl (pH 7.6), 20 mM magnesium chloride, 25 mM potassium chloride and 10 mM DTT. For the annealing of the oligonucleotides corresponding to DNA fragment II, the solution of the oligonucleotides is heated at 95° C. for 2 minutes and then slowly cooled (2-3 hours) to 20° C. Then, for the enzymatic linkage, 2 µl of 0.1 mM DTT, 8 µl of 2.5 mM adenosine triphosphate (pH 7) and 5 µm of T4 DNA ligase (2000 units) are added, and the mixture is incubated at 22° C. for 16 hours.

The gene fragment II is purified by gel electrophoresis on a 10% polyacrylamide gel (without addition of urea, 20×40 cm, 1 mm thick), the marker substance used being φX 174 DNA (from BRL) cut with HinfI, or pBR322 cut with HaeIII.

Gene fragments I, III and IV are prepared analogously, although the "protruding" sequences are, before the annealing, converted into the 5'-phosphates because no ligation step is necessary.

7. Preparation of hybrid plasmids containing gene fragments I, II, III and IV.

a) Incorporation of gene fragment I in pUC18

The commercially available plasmid pUC18 is opened in a known manner using the restriction endo nucleases SalI and XbaI in accordance with the manufacturers' instructions. The digestion mixture is fractionated by electrophoresis in a known manner on a 1% agarose gel, and the fragments are visualized by staining with ethidium bromide. The plasmid band (about 2.6 kb) is then cut out of the agarose gel and removed from the agarose by electroelution. 1 µg of plasmid, opened with XbaI and SalI, is then ligated with 10 ng of DNA fragment I at 16° C. overnight.

b) Incorporation of gene fragment II in pUC18.

In analogy to a), pUC18 is cut open with XbaI and BamHI and ligated with gene fragment II which has previously been phosphorylated at the protruding ends as described in Example 2.

c) Incorporation of gene fragment III in pUC18

In analogy to a), pUC18 is cut open with BamHI and XmaIII and ligated with gene fragment III.

d) Incorporation of gene fragment IV in pUC18

In analogy to a), pUC18 is cut with XmaIII and SalI and ligated with gene fragment IV.

8. Construction of the complete gene and cloning in a pUC plasmid.

a) Transformation and amplification of gene fragments I-IV

The hybrid plasmids obtained in this way are transformed into *E. coli*. For this purpose, the strain *E. coli* K 12 is made competent by treatment with a 70 mM calcium chloride solution, and the suspension of the hybrid plasmid in 10 mM tris-HCl buffer (ph 7.5), which is 70 mM in calcium chloride, is added. The transformed strains are selected as is customary, utilizing the antibiotic resistances or sensitivities conferred by the plasmid, and the hybrid vectors are amplified. After the cells have been killed, the hybrid plasmids are isolated and cut open with the restriction enzymes originally used, and gene fragments I, II, III and IV are isolated by gel electrophoresis.

b) Linkage of gene fragments I, II, III and IV to give the total gene

Subfragments I and II obtained by amplification are linked as follows. 100 ng of each of the isolated fragments I and II are dissolved together in 10 µl of buffer containing 50 mM tris-HCl (pH 7.6), 20 mM magnesium chloride and 10 mM DTT, and this solution is heated at 57° C. for 5 minutes. After the solution has cooled to room temperature, 1 µl of 10 mM adenosine triphosphate (pH 7) and 1 µl of T4 ligase (400 units) are added, and the mixture is incubated at room temperature for 16 hours. After subsequent cutting with the restriction enzymes SalI and BamHI, the desired 312 bp fragment (nucleotides 1-312, SalI-BamHI) is purified by gel electrophoresis on an 8% polyacrylamide gel, the marker substance used being ΦX 174 RF DNA (from BRL) cut with the restriction enzyme HaeIII.

Gene fragments III and IV are linked together in the same way, there being obtained after purification a 246 bp fragment (nucleotides 313-558, BamHI-SalI). The marker used for the gel electrophoresis is pBR322 cut with the restriction enzyme MscI.

To construct the total gene (DNA sequence I), 15 ng of the 312 bp fragment and 12 ng of the 246 bp fragment are ligated, as described above, with 1 µg of the commercially available plasmid pUC18 which has previously been cut open with the restriction enzyme SalI and enzymatically dephosphorylated at the ends. After transformation and amplification (as described in Example 8a), the correct clone having the 558 bp fragment corresponding to DNA sequence I is identified by SalI digestion.

9. Transformation of the hybrid plasmids

Competent *E. coli* cells are transformed with 0.1 to 1 µg of the hybrid plasmid containing DNA sequence III and are plated out on amplicillin-containing agar plates. It is then possible to identify clones which contain the correctly integrated sequences in the plasmid by rapid DNA analysis (Maniatis, loc. cit.).

Fusion of the synthetic gene to regulation signals which are recognized in plants.

The optimized resistance gene which had been provided at the ends with SalI cleavage sites was ligated in the SalI cleavage site of the polylinker sequence of the plasmid pDH51 (Pietrzak et al., Nucleic Acids Res. 14 (1986) 5857). The promoter and terminator of the 35S transcript from cauliflower mosaic virus, which are recognized by the plant transcription apparatus, are located on this plasmid. The ligation of the resistance gene resulted in it being inserted downstream of the promoter and upstream of the terminator of the 35S transcript. The correct orientation of the gene was confirmed by restriction analyses.

The promoter of the ST-LS1 gene from *Solanum tuberosum* (Eckes et al., Mol. Gen. Genet. 205 (1986) 14) was likewise used for the expression of the optimized acetyltransferase gene in plants.

11. Insertion of the resistance gene having the regulation sequence into *Agrobacterium tumefaciens* a) Cointegrate method

The entire transcription unit comprising promoter, optimized resistance gene and terminator (Example 10) was cut out with the restriction enzyme EcoRI and ligated in the EcoRI cleavage site of the intermediary *E. coli* vector pMPK110 (Peter Eckes, Thesis, Univ. Cologne, 1985, pages 91 et seq.). This intermediary vector was necessary for the transfer of the resistance gene with its regulation sequences into the Ti plasmid of *Agrobacterium tumefaciens*. This so-called conjugation was carried out by the method described by Van Haute et al. (EMBO J. 2 (1983) 411). This entailed the gene with its regulation signals being integrated in the Ti plasmid by homologous recombination via the sequences of the standard vector pBR322 which are present in the pMPK110 vector and in the Ti plasmid pGV3850kanR (Jones et al., EMBO J. 4 (1985) 2411).

For this purpose, 50 μl of fresh liquid cultures of each of the *E. coli* strains DH1 (host strain of the pMPK110 derivative) and GJ23 (Van Haute et al., Nucleic Acids Res. 14 (1986) 5857) were mixed on a dry YT-agar plate and incubated at 37° C. for one hour. The bacteria were resuspended in 3 ml of 10 mM MgSO$_4$ and plated out on antibiotic-agar plates (spectinomycin 50 μg/ml: selection for pMPK110; tetracycline 10 μg/ml: selection for R64drd11; kanamycin 50 μg/ml: selective for PGJ28). The bacteria growing on the selective agar plates contained the three plasmids and were grown for the conjugation with *Agrobacterium tumefaciens* in YT liquid medium at 37° C. The Agrobacteria were cultivated in LB medium at 28° C. 50 μl of each bacterium suspension were mixed on a dry YT-agar plate and incubated at 28° C. for 12 to 16 hours. The bacteria were resuspended in 3 ml of 10 mM MgSO$_4$ and plated out on antibiotic plates (erythromycin 0.05 g/l, chloramphenicol 0.025 g/l: selection for the Agrobacterium strain; streptomycin 0.03 g/l and spectinomycin 0.1 g/l: selection for integration of pMPK110 in the Ti plasmid). Only Agrobacteria in which the pMPK110 derivative has been integrated into the bacterial Ti plasmid by homologous recombination are able to grow on these selected plates.

Besides the gene for resistance to the antibiotic kanamycin, which is active in plants and was already present from the outset, the PTC-resistance gene was now also located on the Ti plasmid pGV3850kanR. Before these Agrobacterium clones were used for transformation, a Southern blot experiment was carried out to check whether the desired integration had taken place.

b) Binary vector method

The binary vector system described by Koncz et al. (Mol. Gen. Genet. 204 (1986) 383) was used. The vector pPCV701 described by Koncz et al. (PNAS 84 (1987) 131) was modified in the following way: the restriction enzymes BamHI and HindIII were used to delete from the vector a fragment on which are located, inter alia, the TR1 and TR2 promoters. The resulting plasmid was recircularized. Into the EcoRI cleavage site present on this vector was inserted a fragment from the vector pDH51 which is about 800 base-pairs in length and on which were located the promoter and terminator of the 35S transcript from cauliflower mosaic virus (Pietrzak et al., Nucleic Acids Res. 14 (1986) 5858). The resulting plasmid pPCV801 had a unique SalI cleavage site between the 35S promoter and terminator. The optimized PTC-resistance gene was inserted into this cleavage site. Its expression was now under the control of the 35S transcript regulation sequences.

This plasmid (pPCV801Ac) was transformed into the *E. coli* strain SM10 (Simon et al., Bio/Technology 1 (1983) 784). For the transfer of the plasmid pPCV801Ac into *Agrobacterium tumefaciens*, 50 μl of both the SM10 culture and a C58 Agrobacterium culture (GV3101, Van Larebeke et al., Nature 252 (1974) 169) were mixed with the Ti plasmid pMP90RK (Koncz et al., loc. cit.) as helper plasmid on a dry YT-agar plate, and the mixture was incubated at 28° C. for about 16 hours. The bacteria were then resuspended in 3 ml of 1 mM MgSO$_4$ and plated out on antibiotic plates (rifampicin 0.1 g/l: selection for GV3101, kanamycin 0.025 g/l: selection for pMP90RK, carbenicillin 0.1 g/l: selection for pPCV801Ac). Only Agrobacteria which contained both plasmids (pMP90RK and pPCV801Ac) are able to grow on these plates. Before these Agrobacteria were used for the plant transformation, Southern blotting was carried out to check that the plasmid pPCV801Ac is present in its correct form in the Agrobacteria.

12. Transformation of *Nicotiana tabacum* by *Agrobacterium tumefaciens*.

The optimized resistance gene was transferred into tobacco plants using the so-called leaf disk transformation method.

The Agrobacteria were cultured in 30 ml of LB medium containing the appropriate antibiotics at 28° C., shaking continuously (about 5 days). The bacteria were then sedimented by centrifugation at 7000 rpm in a Christ centrifuge for 10 minutes, and were washed once with 20 ml of 10 mM MgSO$_4$. After a further centrifugation, the bacteria were suspended in 20 ml of 10 mM MgSO$_4$ and transferred into a Petri dish. Leaves of Wisconsin 38 tobacco plants growing on 2MS medium in sterile culture were used for the leaf disk infection. All the sterile cultures were maintained at 25° to 27° C. in a 16 hours light/8 hours dark rhythm under white light.

Tobacco leaves were cut off, and the leaf surfaces were lacerated with sandpaper. After the laceration, the leaves were cut into smaller pieces and dipped in the bacterium culture. The leaf pieces were then transferred to M+S medium and maintained under normal culture conditions for two days. After the 2-day infection with the bacteria, the leaf pieces were washed in liquid M+S medium and transferred to MSC10-agar plates. Transformed shoots were selected on the basis of the resistance to the antibiotic kanamycin which had also been transferred. The first shoots became visible 3 to 6 weeks later. Individual shoots were further cultivated on MSC15 medium in glass jars. In the weeks which followed, some of the shoots which had been cut off developed roots at the site of the cut.

It was also possible to select transformed plants directly on PTC-containing plant media. The presence and the expression of the PTC-resistance gene was demonstrated by DNA analysis (Southern blotting) and RNA analysis (Northern blotting) of the transformed plants.

13. Demonstration of the PTC-resistance of the transformed plants

To check the functioning of the resistance gene in transformed plants, leaf fragments from transformed and non-transformed plants were transferred to M+S nutrient media containing $1 \times 10^{-4}$ M L-PTC. The fragments from non-transformed plants died, while the fragments from transformed plants were able to regenerate new shoots. Transformed shoots took root and grew without difficulty on M+S nutrient media containing $1 \times 10^{-3}$ M L-PTC. Transformed plants were, from sterile conditions, potted in soil and sprayed with 2 kg/ha and 5 kg/ha PTC. Whereas non-transformed plants did not survive this herbicide treatment, transformed plants showed no damage brought about by the herbicide. The appearance and growth behavior of the sprayed transformed plants was at least as good as that of unsprayed control plants.

14. Acetyltransferase assay to demonstrate acetylation of PTC in transgenic PTC-resistant plants.

About 100 mg of leaf tissue from transgenic PTC-resistant tobacco plants or from non-transformed tobacco plants were homogenized in a buffer composed of: 50 mM tris-HCl, pH 7.5; 2 mM EDTA; 0.1 mg/ml leupeptin; 0.3 mg/ml bovine serum albumin; 0.3 mg/ml DTT; 0.15 mg/ml phenylmethylsulfonyl fluoride (PMSF).

After subsequent centrifugation, 20 µl of the clear supernatant were incubated with 1 µl of 10 mM radio-labelled D,L-PTC and 1 µl of 100 mM acetyl-CoA at 37° C. for 20 minutes. 25 µl of 12% trichloroacetic acid were then added to the reaction mixture, followed by centrifugation. 7 µl of the supernatant were transferred to a thin-layer chromatography plate and subjected to ascending development twice in a mixture of pyridine : n-butanol : acetic acid : water (50:75:15:60 parts by volume). PTC and acetyl-PTC were separated from one another in this way, and could be detected by autoradiography. Non-transformed plants exhibited no conversion of PTC into acetyl-PTC, whereas transgenic resistant plants were capable of this.

TABLE I

DNA Sequence 1

IleTrpSerAspValLeuGlyAlaGlyProValLeuProGlyAspAspPheSerLeuGlyGlyThrSerIle
AspLeuGluArgProGlyGlyArgSerGlyAlaAlaArgGlyArgLeuLeuProArgAlaArgHisLeuHis
ArgSerGlyAlaThrSerTrpGlyProValArgCysCysProGlyThrThrSerSerProSerAlaAlaProPro
AGATCTGGAGCGACGTCCTGGGGGCCGGTCCTGCCCGGGACGACTTCTTCTCCCTCGGCGGCACCTCCA  75
TCTAGACCTCGCTGCAGGAGCCCCCGGCCAGGACGGGCCCCTGCTGAAGAAGAGGGAGCCGCCGTGGAGT
SerArgSerArgArgGlyProProArgAspProAlaAlaArgProArgSerArgArgProArgGlyArgCysArgTrp
AspProAlaValAspGlnProGlyThrArgHisGlnGlyProValValGluGluValGlyAlaAlaGlyGlyAsp
IleGlnLeuSerThrArgProAlaProGlyThrSerGlyProSerSerLysLysGlyProProValGluMet

SerAlaLeuArgValValSerArgIleArgLysGluArgIleGlyValProLeuArgLeuAlaValIlePheGluThr
LeuGlyValAlaGlyGlyLeuAlaHisProGlnGlyThrArgArgAlaThrProAlaArgArgAspLeuArgAsp
SerArgArgCysGlyTrpSerArgAlaSerAlaArgAsnSerAlaCysHisSerGlySerProOP SerSerArg
TCTCGGCGTTGCGGGTGCTCTCGCGCATCCGCAAGGAACTCGGCGTGCCACTCCGGCTCGCCGTGATCTTCGAGA  150
AGAGCCGCAACGCCCACCAGAGCGCGTAGGCGTTCCTTGAGCCGCACGGTGAGGCGCACTAGAAGCTCT
ArgProThrAlaProProArgAlaCysGlyCysProValArgArgAlaValGlyAlaArgArgSerArgSer
ArgArgGlnProHisAspArgAlaAspAlaLeuPheGluAlaHisTrpGluProGluGlyHisAspGlyLeuArg
GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro
AlaValProGlySerGlyGlyGlyArgIleArgThrProArgThrGluGlyAspValValLysArgCysProProPro
ArgArgProTrpLysArgTrpProAsnProTyrSerAlaAsnOP ArgGlyArgSerLysGlyValProAlaThr
CGCCGTGGGTGGAAGCGGTGGCCGAATCCGTACTCCGCGAACTGAAGGGGACGTAGTAAAGAGGTGCCCGCACC  225
GCGGCAGGGACCCTTCGCCACCCGACGCTTAGCATGAGGCGCTTGACTTCCCCTGACTCATCATTTCTCCACGGCGGTGG
AlaThrGlyProLeuProArgIleArgValGlyArgValSerProSerThrThrPheLeuHisGlyGly
ArgGlyGlnPheArgHisGlyTyrGluAlaPheGlnLeuProArgLeuLeuSerThrGlyAlaValArg
GlyAspArgSerAlaThrAlaSerArgSerPheProValTyrTyrLeuProAlaArgTrpGly

LeuSerGlnAsnThrGluGlyProHisValSerProGluArgArgProValGluIleArgProAlaThrAla
AlaPheArgLeuGluHisArgArgLysThrThrArgGluProArgThrThrProGlyArgAspProSerArgHisArg
ArgPheArgArgThrProLysGluAspHisThrOP AlaGlnAsnAspAlaArgSerValProProPro
CGCTTTCGCAGGAACACCGAAGGAGCCACACGTAGCACTCGGGTCTTGCTCGGGGCCAGCTCTAGGCAGGCGGTGGC  300
GCGAAAGCGTCTTGTGGCTTCCTTCGTGTGTGCACTGGGTGTCCTGGCCAGCAGTCGGCCGGCCATGCCCGGCACCG
AlaLysAlaSerCysArgLeuPheValAlaSerGlyLeuValValGlyProArgSerGlyAspArgTrpArg
LysArgLeuValGlyPheSerSerTrpValHisAlaTrpPheSerAlaArgAspLeuArgThrGlyGlyGly
SerGluCysPheValSerProLeuGlyCysThrLeuGlySerArgArgGlyThrSerIleArgGlyAlaValAla

AlaAspMetAlaAlaValCysAspIleValAsnHisTyrIleGluThrSerThrValAsnPheArgThrGluPro
ArgArgHisGlyGlyGlyLeuArgHisArgGlnSerLeuHisArgAspGluHisGlyGlnLeuProTyrGlyAla
ProProThrTrpArgArgSerAlaThrSerSerIleThrThrSerSerArgArgAlaArgSerThrSerValArgSer
CCGCGACACATGGCGGCGGTCTGCGACATCGTCAATCACTACATCGAGACGAGCACGGTCAACTTCCGTACGGAGC  375
GGCGGCTGTACCGCCGCAGCAGCTGTAGCAGTTAGTGATGATGTAGCTCTGCTCGTGCCAGTTGAAGGCATGCCTCG
ArgArgCysProProArgArgCysArgOP AspSerCysArgSerCysProOP SerGlyTyrProAla
GlyValHisArgArgProAlaValAspAlaIleValValAspLeuArgAlaArgAspValGluThrArgLeuArg
AlaSerMetAlaAlaThrGlnSerMetThrLeuOP AM MetSerValLeuValThrLeuValArgValSerGly

GlnThrProGlnGluTrpIleAspIleLeuGlnAspArgTyrProTrpLeuValAlaGluValGlu
AlaAspSerAlaGlyValAspArgProGlyAlaProProGlyProLeuProLeuAlaArgArgGlyGly
ArgArgLeuArgArgSerAlaGlySerThrThrThrProSerAlaSerArgThrAlaThrProGlySerProValTrp
CGCAGACTCCGCAGGAGTGGATCGACGACCTGCAGGACCGCTACCCCTGGCTCGTCGCCGAGGTGG  450
GCGTCTGAGGCGTCCTCACCTAGCTGCTGGACGTCCTGGCGATGGGGACCGAGCAGCAGGCTCCACC
AlaSerGluAlaProThrSerArgArgGlyProAlaGlyProGlySerGlyArgAlaArgArgProPro
LeuSerArgLeuProAspValGlnLeuAlaGlnLeuAlaValGlyProGlySerArgAlaValGlyProGluLeuHisLeu

TABLE I-continued

DNA Sequence I

CysValGlyCysSerHisIleSerSerArgArgSerArgTrpSerArgAM GlyGlnSerThrAlaSerThrSer

GlyValValAlaGlyIleAlaTyrAlaGlyProTrpLysAlaArgAsnAlaTyrAspTrpThrValGluSerThr
GlyArgArgArgArgHisArgLeuArgArgProLeuGluGlyProGlnArgLeuAspArgArgValAsp
ArgAlaSerSerProAlaSerProThrProAlaProGlyArgProAlaThrProThrThrGlyProSerArg
AGGGCGTCGTCGCCGGCATCGCCTACGCGGGCCGGCCCCTGGAAGGCCCGAACGCCTACGACTGGACCGTCGAGTCGA     525
TCCCGCAGCAGCGGCCGTAGCGGATGCGGCCGGGACCTTCCGGGCGTTGCGGATGCTGACCTGGCAGCTCAGCT
ProArgArgArgArgCysArgArgArgGlyArgSerProGlyCysArgArgArgSerArgArgSerArgThrSer
AlaAspAspAlaGlyAlaAspGlyValAlaGlyProLeuGlyAlaGlyValValProGlyAspLeuArgArg
ProThrThrAlaProMetAlaAM AlaProGlyGlnPheAlaAlaArgLeuAlaAM SerGlnValThrSerAspVal

ValTyrValSerHisArgHisGlnArgLeuValGlySerThrLeuTyrThrHisLeuLeuLysSerMetGlu
GlyValArgLeuProProAlaArgThrGlyLeuHisProLeuHisProProAlaGluValHisGly
ArgCysThrSerProThrGlyThrSerGlySerAspTrpAlaProProSerThrProThrCysOP SerProTrp
CGGTGTACGTCTCCCACCGGCACCAGCGGCTCGGACTGGGCTCCACCCTCTACACCCACCTGCTGAAGTCCATGG     600
GCCACATGCAGAGGGTGGCCGTGCGGCCAGACCTGGTCGCCGAGCCTGACCGAGGTGGGAGATGTGGGTGAGTACC
ProThrArgArgGlyAlaGlyAlaAlaArgValProSerTrpGlyArgCysArgCysGlyGlyAlaSerThrTrpPro
HisValAspGlyValProValLeuProGluSerGlnAlaGlyGlyGluValGlyValGlnGlnLeuGlyHisLeu
ThrTyrThrGluThrArgCysTrpArgSerProSerProGluValArgAM ValTrpArgSerPheAspMetSer

AlaGlnGlyPheLysSerValValAlaValIleGlyLeuProAsnAspProSerValArgLeuHisGluAlaLeu
GlyProGlyLeuGlnGluArgGlyArgArgHisArgThrAlaGlnArgProGluArgAlaProAlaArgGlyAla
ProArgAlaSerArgAlaTrpSerProSerSerAspCysProThrThrArgAlaCysAlaCysThrArgArg
AGGCCCCAGGCGCTTCAAGAGCGTGTGGCCGTCATCGGACTGCCCAACGACCCGAGCGTGCGCCTGCACGAGGCGC     675
TCCGGGTCCCGAAGTTCTCGCACCAGCGGCAGTAGCCTGACGGGTTGCTGGCTGCACGGCGACGTGCTCCGCG
ProGlyProSerOP SerArgProArgProArgOP ArgValAlaTrpArgGlySerArgAlaGlyAlaArgProAla
GlyLeuAlaGluLeuAlaHisAspAspSerGlnGlyValValArgAlaHisAlaGlnLeuArgArgGlu
AlaTrpProLysLeuThrThrAlaThrMetProSerGlyLeuSerGlyLeuThrArgArgCysSerAlaSer

GlyTyrThrAlaArgGlyThrLeuArgAlaAlaGlyTyrLysHisGlyGlyTrpLysHisGlyValGlyPheTrpGln
ArgIleHisArgAlaArgAlaAspAlaAlaGlySerArgLeuGlnAlaArgLeuArgArgGlyValLeuAla
SerAspThrProArgAlaGlyArgCysGlyGlnProAlaThrSerThrGlyAlaGlyThrTrpGlySerGly
TCGGATACACCGCGCGCGGGACGCTGCGGCAGCACGCTACAAGCACGGGGGCTGGCACGACGTGGGGTTCTGGC     750
AGCCTATGTGGCGCGCGCCCTGCGACGCCGTCGCGACCGATGTTCGTGCCCCGACCGTGCTGCACCCCAAGACCG
ArgIleCysArgAlaArgSerAlaAlaProLeuArgSerCysAlaValProSerAlaArgArgProThrArgAla
SerValGlyArgAlaProArgGlnProCysGlyAlaValLeuValProAlaProValLeuHisProGluProLeu
ProTyrValAlaArgProValSerArgAlaAlaProAM LeuCysProProGlnCysSerThrProAsnGlnCys

ArgAspPheGluProAlaProArgProValArgProValThrGlnIle
AlaArgLeuArgAlaAlaGlyProArgProArgProAlaArgHisThrAsp
SerAlaThrSerSerCysArgProArgProAlaProSerGlyProSerHisArgSer
AGCGCGACTTCGAGCTGCCGGCCCCGCGCCCCGTCCGGCCCGTCACACAGATCT                             807
TCGCGCTGAAGCTCGACGCCGGGGCTGGGGCGCGGGGCAGGCCGGGCAGTGTGTCTAGA
AlaArgSerArgAlaAlaProGlyGlyGlyArgGlyArgArgOP ValSerArg
AlaValGluLeuGlnArgGlyArgGlyAlaGlyAspProGlyAspCysLeuAsp
ArgSerLysSerGlyAlaGlyGlyArgGlyThrArgGlyThrValCysIle

TABLE II

DNA Sequence II

1 AGATCTGGAGCGACGTCCTGGGGGCCGGTCCGGTGCTGCCCGGGGACGACTTCTTCTCCC
  TCTAGACCTCGCTGCAGGACCCCCGGCCAGGCCACGACGGGCCCCTGCTGAAGAAGAGGG

1 BGLII XHOII, 2 DPNI SAU3A, 5 GSUI, 12 AATII ACYI, 13 MAEII,
  17 APYI ECORII, 26 RSRII, 27 AVAII, 35 BBVI, 39 AVAI NCII
  SMAI, 40 NCII, 52 MBOII, 59 MNLI,

61 TCGGCGGCACCTCCATCTCGGCGTTGCGGGTGGTCTCGCGCATCCGCAAGGAACTCGGCG
   AGCCGCCGTGGAGGTAGAGCCGCAACGCCCACCAGAGCGCGTAGGCGTTCCTTGAGCCGC

66 HGICI, 70 MNLI, 97 FNUDII, 100 SFANI, 101 FOKI,

121 TGCCACTCCGGCTCGCCGTGATCTTCGAGACGCCGTCCCTGGAAGCGGTGGCCGAATCCG
    ACGGTGAGGCCGAGCGGCACTAGAAGCTCTGCGGCAGGGACCTTCGCCACCGGCTTAGGC

122 BGLI, 140 DPNI SAU3A, 142 MBOII, 149 ACYI HGAI TTH111I,
    158 APYI ECORII, 169 CFRI GDIII, 174 HINFI, 180 RSAI,

181 TACTCCGCGAACTGAAGGGGACGTAGTAAAGAGGTGCCCGCCACCCGCTTTCGCAGAACA
    ATGAGGCGCTTGACTTCCCCTGCATCATTTCTCCACGGGCGGTGGGCGAAAGCGTCTTGT

185 FNUDII, 201 MAEII, 211 MNLI, 213 HGICI, 214 SDUI,

241 CCGAAGGAAGACCACACGTGAGCCCAGAACGACGCCCGGTCGAGATCCGTCCCGCCACCG
    GGCTTCCTTCTGGTGTGCACTCGGGTCTTGCTGCGGGCCAGCTCTAGGCAGGGCGGTGGC

247 MBOII, 254 AFLIII, 255 PMACI, 256 MAEII, 260 HGIJII SDUI,
    271 ACYI HGAI, 275 NCII, 283 XHOII, 284 BINI DPNI SAU3A,

301 CCGCCGACATGGCGGCGGTCTGCGACATCGTCAATCACTACATCGAGACGAGCACGGTCA
    GGCGGCTGTACCGCCGCCAGACGCTGTAGCAGTTAGTGATGTAGCTCTGCTCGTGCCAGT

303 BGLI, 308 NLAIII, 324 TTH111I, 350 HGIAI SDUI, 357 HINCI
    I,

361 ACTTCCGTACGGAGCCGCAGACTCCGCAGGAGTGGATCGACGACCTGGAGCGCCTCCAGG
    TGAAGGCATGCCTCGGCGTCTGAGGCGTCCTCACCTAGCTGCTGGACCTCGCGGAGGTCC

367 RSAI, 380 HINFI, 394 BINI, 395 DPNI SAU3A, 404 APYI ECOR
    II, 405 GSUI, 409 HAEII, 413 MNLI, 414 GSUI, 416 APYI ECORII,
    419 AVAII,

421 ACCGCTACCCCTGGCTCGTCGCCGAGGTGGAGGGCGTCGTCGCCGGCATCGCCTACGCCG
    TGGCGATGGGGACCGAGCAGCGGCTCCACCTCCCGCAGCAGCGGCCGTAGCGGATGCGGC

430 APYI ECORII, 444 MNLI, 450 MNLI, 453 ACYI, 454 HGAI, 462
    NAEI, 466 SFANI, 477 NAEI,

481 GCCCCTGGAAGGCCCGCAACGCCTACGACTGGACCGTCGAGTCGACGGTGTACGTCTCCC
    CGGGGACCTTCCGGGCGTTGCGGATGCTGACCTGGCAGCTCAGCTGCCACATGCAGAGGG

484 APYI ECORII, 511 AVAII, 519 HINFI, 521 ACCI HINCII SALI,
    530 RSAI, 532 MAEII,

541 ACCGGCACCAGCGGCTCGGACTGGGCTCCACCCTCTACACCCACCTGCTGAAGTCC ↑
    TGGCCGTGGTCGCCGAGCCTGACCCGAGGTGGGAGATGTGGGTGGACGACTTCAGGT ↑

544 HGICI, 549 NSPBII, 563 HGIJII GDUI, 572 MNLI, 578 TAQII,
    583 BSPMI, 595 NCOI STYI, 596 NLAIII, 600 MNLI,

601 AGGCCCAGGGCTTCAAGAGCGTGGTCGCCGTCATCGGACTGCCCAACGACCCGAGCGTGC
    TCCGGGTCCCGAAGTTCTCGCACCAGCGGCAGTAGCCTGACGGGTTGCTGGGCTCGCACG

605 APYI ECORII, 650 AVAI,

661 GCCTGCACGAGGCGCTCGGATACACCGCGCGCGGGACGCTGCGGGCAGCCGGCTACAAGC
    CGGACGTGCTCCGCGAGCCTATGTGGCGCGCGCCCTGCGACGCCCGTCGGCCGATGTTCG

669 MNLI, 671 HAEII, 686 FNUDII, 687 BSSHII, 688 FNUDII, 690
    FNUDII, 695 HGAI, 698 BBVI, 705 BBVI, 708 NAEI, 716 TTH111I
    I,

721 ACGGGGGCTGGCACGACGTGGGGTTCTGGCAGCGCGACTTCGAGCTGCCGGCCCCGCCCC
    TGCCCCCGACCGTGCTGCACCCCAAGACCGTCGCGCTGAAGCTCGACGGCCGGGGCGGGG

732 DRAIII, 736 MAEII, 749 BBVI, 753 FNUDII, 763 ALUI, 764 B
    BVI, 767 NAEI,

781 GCCCCGTCCGGCCCGTCACACAGATCT

TABLE II-continued

DNA Sequence II

CGGGGCAGGCCGGGCAGTGTGTCTAGA

795 MAEIII, 802 BGLII XHOII, 803 DPNI SAU3A,

TABLE III

Amino acid and DNA sequence III

```
         MET SER PRO GLU ARG ARG PRO VAL GLU ILE ARG PRO ALA THR ALA ALA ASP MET ALA ALA VAL CYS ASP ILE VAL ASN HIS TYR
      TC GAC ATG TCT CCG GAG AGG AGA CCA GTT GAG ATT AGG CCA ACA GCT GCA GCT GAT ATG GCC GCG GTT TGT GAT ATG GTT AAC CAT TAC
      G TAC AGA GGC CTC TCC TCT CCT CAA CTC TAA TCC GGT CGT CGA CGT CTA CAC CGG CGC CAA ACA CTA TAG CAA TTG GTA ATG
                                                                  100

ILE GLU THR SER THR VAL ASN PHE ARG THR GLU PRO GLN THR PRO GLN GLU TRP ILE ASP ASP LEU GLU ARG LEU GLN ASP ARG TYR PRO
      ATT GAG ACG TCT ACA GTG AAC TTT AGG ACA GAG CCA CAA ACA CCA CAA GAG TGG ATT GAT GAT CTA GAG AGG TTG CAA GAT AGA TAC CCT
      TAA CTC TGC AGA TGT CAC TTG AAA TCC TGT CTC GGT GTT TGT GGT GTT CTC ACC TAA CTA CTA GAT CTC TCC AAC GTT CTA TCT ATG GGA

TRP LEU VAL ALA GLU VAL GLU GLY VAL VAL ALA GLY ILE ALA TYR ALA GLY PRO TRP LYS ALA ARG ASN ALA TYR ASP TRP THR VAL GLU
      TGG TTG GTT GCT GAG GTT GAG GGT GTT GTG GCT GGT ATT GCT TAC GGG CCC TGG AAG GCT AGG AAC GCT TAC GAT TGG ACA GTT GAG
      ACC AAC CGA CTC CAA CTC CCA CAA CAC CGA CCA TAA CGA ATG CCC GGG ACC TTC CGA TCC TTG CGA ATG CTA ACC TGT CAA CTC
                                        200

SER THR VAL TYR VAL SER HIS ARG HIS GLN ARG LEU GLY SER THR LEU TYR THR HIS LEU LEU LYS SER MET GLU ALA GLN GLY
      AGT ACT GTT TAC GTG TCA CAT AGG CAT CAA AGG TTG GGC CTA GGA TCC ACA CAT TTG TAC ACA CAT TTG CTT AAG TCT ATG GAG GCG CAA GGT
      TCA TGA CAA ATG CAC AGT GTA TCC GTA GTT TCC AAC CCG GAT CCT AGG TGT AAC ATG TGT AGA TTC AAC GAA TTC AGA TAC CTC CGC GTT CCA

PHE LYS SER VAL VAL ALA VAL ILE GLY LEU PRO ASN ASP PRO SER VAL ARG LEU HIS GLU ALA LEU GLY TYR THR ALA ARG GLY THR LEU
      TTT AAG TCT GTT GTT GCT GTT ATA GGC CTT CCA AAC GAT CCA TCT AGA GTT CAT GAG CTC TTG GGA TAC ACA GCC CGG GGT ACA TTG
      AAA TTC AGA CAC CAA CGA CAA TAT CCG GAA GGT TTG CTA GGT AGA TCT CAA GTA CTC GAG AAC CCT ATG TGT CGG GCC CCA TGT AAC
                                                         300

ARG ALA ALA GLY TYR LYS HIS GLY GLY PHE TRP HIS ASP VAL GLY PHE GLU LEU PRO ALA ASP PHE GLN ARG ASP PRO ARG PRO VAL ARG
      CGC GCT GCA GCT GGA TAC AAG CAT GGT GGA TGG CAT GAT GTT GGT TTT GAG TTG CCA GCA GAT TTT CAA AGG GAT CCA AGG CCA GTT AGG
      GCG CGT CGA CGA CCT ATG TTC GTA CCA CCT ACC GTA CTA CAA CCA AAA ACT CTC AAC GGT CGT CTA AAA GTT TCC CTA GGT TCC GGT CAA TCC
                                                                                400                                             500

PRO VAL THR GLN ILE ...
      CCA GTT ACC CAG ATC TGA G
      GGT CAA TGG GTC TAG ACT CAG CT
```

TABLE IV

Amino acid and DNA sequence IV

```
              Ia
MET SER PRO GLU ARG ARG PRO VAL GLU ILE ARG PRO ALA THR ALA ALA ASP MET ALA ALA VAL CYS ASP ILE VAL ASN HIS TYR
TC GAC ATG TCT CCG GAG AGG AGA CCA GTT GAG ATT AGG CCA GCT ACA GCA GCT GAT ATG GCC GTT TGT GAT ATC GTT AAC CAT TAC
G TAC AGA GGC CTC TCT CCT GGT CAA ATA TAA TCC GGT CGA TGT CGT CGA ACA CTA TAG GCA CAA ACA CTA TAG CAA TTG GTA ATG
                                                                                                              Ib

ILE GLU THR SER THR VAL ASN PHE ARG THR GLU PRO GLN THR PRO GLN GLU TRP ILE ASP ASP|LEU GLU ARG LEU GLN ASP ARG TYR PRO
ATT GAG ACG TCT ACA GTG AAC TTT AGG ACA GAG CCA CAA ACA CCA CAA GAG TGG ATT GAT GAT|CTA GAG AGG TTG CAA GAT AGA TAC CCT
TAA CTC TGC AGA TGT CAC TTG AAA TCC TGT CTC GGT GTT TGT GGT GTT CTC ACC TAA CTA CTA|GAT CTC TCC AAC GTT CTA TCT ATG GGA
                                              Ib                                    IIa                          IIb

TRP LEU VAL ALA GLU GLY VAL VAL ALA GLY ILE|ALA TYR ALA ALA PRO TRP LYS ALA ARG ASN ALA TYR ASP TRP THR VAL GLU
TGG TTG GTT GCT GAG GGT GTT GTG GCT GGT ATT|GCT TAC GCT GCT CCC TGG AAG GCT AGG AAC GCT TAC GAT TGG ACA GTT GAG
ACC AAC CAA CGA CTC CCA CAA CAC CGA CCA TAA|CGA ATG CGA CGA GGG ACC TTC CGA TCC TTG CGA ATG CTA ACC TGT CAA CTC
                         IIb                 IIc                                                                IId

SER THR VAL TYR VAL SER HIS ARG HIS GLN ARG LEU GLY LEU GLY|SER THR LEU TYR THR HIS LEU LEU LYS SER MET GLU ALA GLN GLY
AGT ACT GTT TAC GTG TCA CAT AGG CAT CAA AGG TTG GGC CTA GGA|TCC ACA TTG TAC ACA CAT TTG CTT AAG TCT ATG GAG GCG CAA GGT
TCA TGA CAA ATG CAC AGT TGT TCC GTA TCC GTA GTT TCC AAC CCG GAT C CT|AGG TGT AAC ATG TGT GTA AAC GAA TTC AGA TAC CTC CGC GTT CCA
             IId                                                IIIa                                        IIIb

PHE LYS SER VAL VAL ALA VAL ILE GLY LEU PRO ASN ASP ASN|PRO SER VAL ARG LEU HIS GLU ALA LEU GLY TYR THR LEU|ARG GLY THR LEU
TTT AAG TCT GTT GTT GCT GTT ATA GGC CTT CCA AAC GAT CTA|GGT CGT AGG TTG CAT GAG GCT TTG GGA TAC ACA GCC|CGG GGT ACA TTG
AAA TTC AGA CAA CAA CGA CAA TAT CCG GAA CGT TTG CTA GAT|CCA GCA TCC AAC CGA CTC CGA AAC CCT ATG TGT CGG|GCC CCA TGT AAC
                                                    IIIb                                            IVa                    IVb

ARG ALA ALA GLY TYR LYS HIS ASP VAL GLY PHE TRP GLN ARG ASP PHE GLU LEU PRO ALA PRO PRO ARG PRO VAL ARG
CGC GCA GCT GGA TAC AAG CAT GAT GTT GGT TTT TGG CAA AGA GAT TTC GAG TTG CCA GCT CCT CCA AGG CCA GTT CGA
GCG CGT CGA CCT ATG TTC GTA CTA CAA CCA AAA ACC GTT TCT CTA AAG CTC AAC GGT CGA GGA GGT TCC GGT CAA TCC

PRO VAL THR GLN ILE ...
CCA GTT ACC CAG ATC TGA G
GGT CAA TGG GTC TAG ACT CAG CT
       IVb
```

We claim;

1. An isolated resistance gene coding for the protein of amino acid sequence III, which gene is adapted to codon usage in plants so that it is expressed in plant cells at a level sufficient to confer resistance to phosphinothricin in said plant cells.

2. The resistance gene as claimed in claim 1, having DNA sequence III (nucleotide positions 9–554).

3. A gene structure having DNA sequence III operatively linked to regulation and expression signals active in plants so that it is expressed in plant cells at a level sufficient to confer resistance to phosphinothricin in said plant cells.

4. A vector containing a gene structure as claimed in claim 3.

5. A plant or bacterial host cell containing a vector as claimed in claim 4.

6. A plant cell containing a gene as claimed in claim 1.

7. A plant cell containing a gene as claimed in claim 2.

8. A plant cell containing a gene as claimed in claim 3.

9. Plants and their propagules containing a gene as claimed in claim 1.

10. Plants, their parts and seeds containing a gene as claimed in claim 2.

11. Plants, and their propagules containing a gene as claimed in claim 3.

12. A process for generating phosphinothricin resistant plant cells, plants, and their propagules which comprises transforming plant cells with the gene as claimed in claim 1, and regenerating the transformed plant cells to plants which produce propagules.

13. A process for generating phosphinothricin resistant plant cells, plants, and their propagules which comprises transforming plant cells with the gene as claimed in claim 2, and regenerating the transformed plant cells to plants which produce propagules.

14. A process for generating phosphinothricin resistant plant cells, plants and their propagules which comprises transforming plant cells with the gene structure as claimed in claim 3, and regenerating the transformed plant cells to plants which produce propagules.

* * * * *